(12) United States Patent
Deo et al.

(10) Patent No.: US 8,420,856 B2
(45) Date of Patent: Apr. 16, 2013

(54) PROCESS FOR PREPARATION OF TERIFLUNOMIDE

(75) Inventors: Keshav Deo, Vadodara (IN); Samir Patel, Vadodara (IN); Snehal Dhol, Vadodara (IN); Sunil Sanghani, Vadodara (IN); Vishal Ray, Vadodara (IN)

(73) Assignee: Alembic Ltd., Gujarat (ID)

( * ) Notice: Subject to any disclaimer, the term of this patent is extended or adjusted under 35 U.S.C. 154(b) by 299 days.

(21) Appl. No.: 13/001,250

(22) PCT Filed: Jul. 15, 2009

(86) PCT No.: PCT/IB2009/053061
§ 371 (c)(1),
(2), (4) Date: Dec. 23, 2010

(87) PCT Pub. No.: WO2010/013159
PCT Pub. Date: Feb. 4, 2010

(65) Prior Publication Data
US 2011/0105795 A1    May 5, 2011

(30) Foreign Application Priority Data
Jul. 29, 2008 (IN) .......... 1629/MUM/2008

(51) Int. Cl.
*C07C 231/02* (2006.01)
*C07C 233/05* (2006.01)
*C07C 255/01* (2006.01)

(52) U.S. Cl.
USPC ............ 564/136; 564/200; 564/202; 558/392

(58) Field of Classification Search ................. 564/136, 564/200, 202; 558/392
See application file for complete search history.

(56) References Cited

FOREIGN PATENT DOCUMENTS
GB    1571990    7/1980

OTHER PUBLICATIONS

Faragher et al, Journal of Labelled Compounds & Radiopharmaceuticals,46(7), 613-622, 2003.*
Kallumpurath Deepa, et al., Synthesis and Characterization of Transition Metal Complexes of α-Bromo- and ω-Bromoacetoacetanilide Semicarbazones; Synthesis and Reactivity in Inorganic, Metal-Organic, and Nano-Metal Chemistry, vol. 34, Issue 3, Mar. 2004, 11 Pages.

* cited by examiner

*Primary Examiner* — Shailendra Kumar
(74) *Attorney, Agent, or Firm* — Sughrue Mion, PLLC

(57) ABSTRACT

The present invention provides a process for preparing Teriflunomide of formula (I).

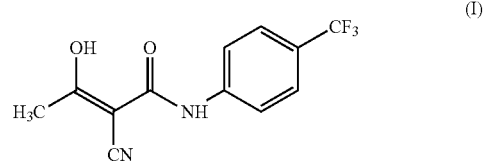

7 Claims, No Drawings

PROCESS FOR PREPARATION OF TERIFLUNOMIDE

This application is a 371 of PCT/IB09/53061, filed Jul. 15, 2009.

FIELD OF THE INVENTION

The present invention provides a process for preparing Teriflunomide of formula (I).

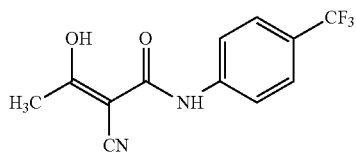

BACKGROUND OF THE INVENTION

The chemical name of Teriflunomide is 2-cyano-3-hydroxy-N-[4-(trifluoromethyl)phenyl]-2-butenamide and formula is $C_{12}H_9F_3N_2O_2$ and molecular weight is 270.207.

Teriflunomide is used as Immunosuppressant. It acts as tyrosine kinase inhibitor. It is used in treatment of rheumatoid arthritis, autoimmune disease and multiple sclerosis.

Teriflunomide was first disclosed and claimed in U.S. Pat. No. 5,679,709 but this application does not mention the process of preparation.

U.S. Pat. No. 5,494,911 discloses process for preparation of Teriflunomide in Example-4 as shown in given below scheme-I.

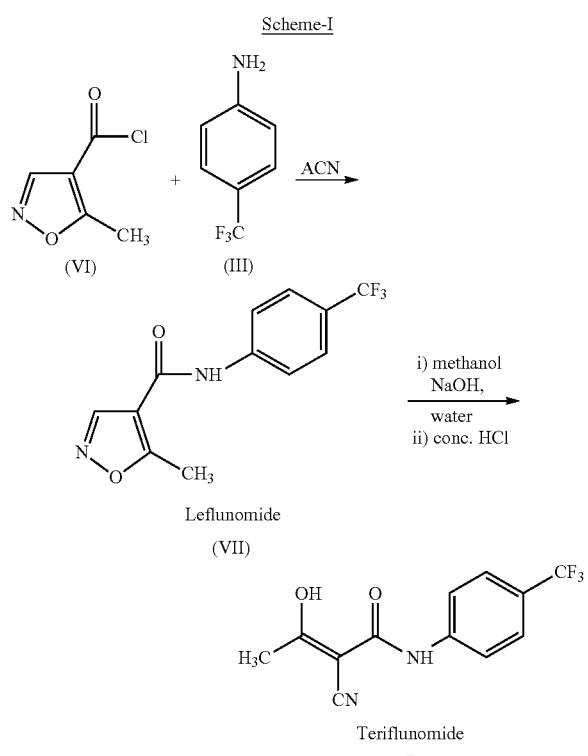

The process involves reacting 5-methylisoxazole-4-carbonyl chloride (VI) with 4-trifluoromethylaniline (III) in acetonitrile to give leflunomide (VII). The subsequent hydrolysis with aqueous sodium hydroxide solution in methanol gives Teriflunomide (I).

U.S. Pat. No. 5,990,141 discloses process for preparation of Teriflunomide as shown in given below scheme-II.

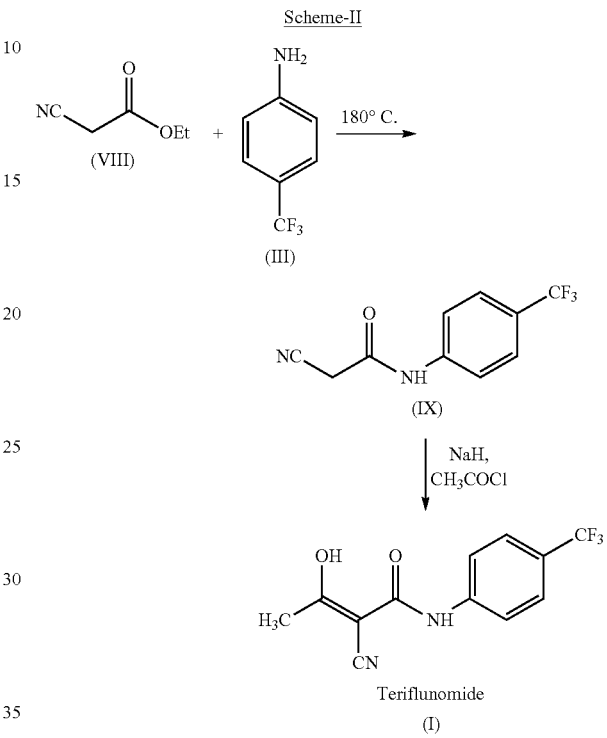

The process involves reacting 4-trifluoromethyl aniline (III) with cyanoacetic acid ethyl ester (VIII) to give cyanoacet-(4-trifluoromethyl)-anilide (IX). This compound is further reacted first with sodium hydride in acetonitrile and then with acetylchloride in THF to give Teriflunomide (I).

U.S. Pat. No. 6,365,626 discloses process for preparation of Teriflunomide in FIG. 19 which is as given in below scheme-III.

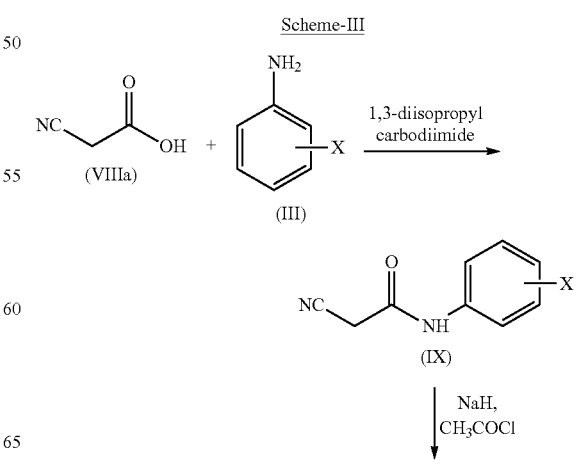

-continued

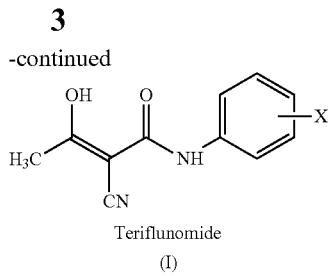
Teriflunomide
(I)

X = para CF₃

The process involves reacting 4-trifluoromethyl aniline (III) with cyanoacetic acid (VIIIa) to give compound of formula (IX). This compound is further reacted first with sodium hydride and then with acetylchloride to give Teriflunomide (I)

All the above mentioned process requires chromatographic purification which in turn results in low yield.

It is therefore, a need to develop a process which not only overcomes the disadvantages of the prior art but also be economical, operationally simple and industrially applicable.

Present inventors have directed their research work towards developing a process for the preparation of Teriflunomide which is devoid of the above disadvantages. The present inventor made a novel process which not only reduce number of steps but is also feasible at commercial scale.

SUMMARY OF THE INVENTION

It is therefore an object of the present invention to provide a process for the preparation of Teriflunomide.

Another object of the present invention is to provide a process for preparation of Teriflunomide which is simple and easy to handle at an industrial scale.

Accordingly, present invention provides a process for preparation of Teriflunomide (I)

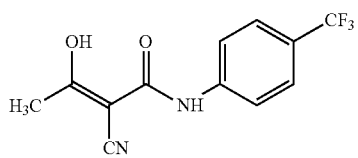
(I)

comprising steps of:
condensing ethylacetoacetate (II)

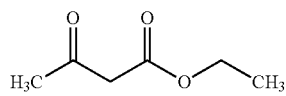
(II)

with 4-trifluoromethyl aniline (III) in a solvent

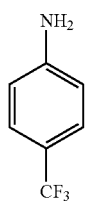
(III)

to give 3-oxo-N-(4-trifluoromethylphenyl)butanamide (IV);

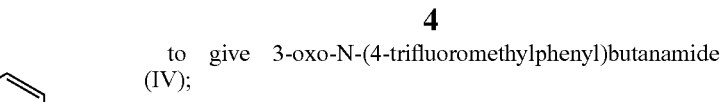
(IV)

(i) brominating 3-oxo-N-(4-trifluoromethylphenyl)butanamide (IV) with brominating agent optionally in presence of solvent to give 2-bromo-3-oxo-N-[4-(trifluoromethyl)phenyl]butanamide (V);

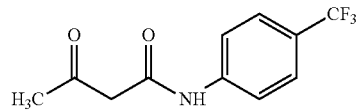
(V)

(ii) reacting 2-bromo-3-oxo-N-[4-(trifluoromethyl)phenyl]butanamide (V) with alkali cyanide in the presence of a solvent to give Teriflunomide (I).

The present invention provides a novel compound of formula (V)

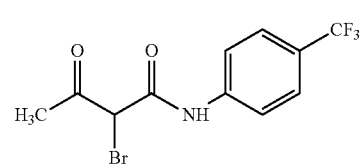
(V)

DETAILED DESCRIPTION OF THE INVENTION

Present invention provides a process for preparation of Teriflunomide (I)

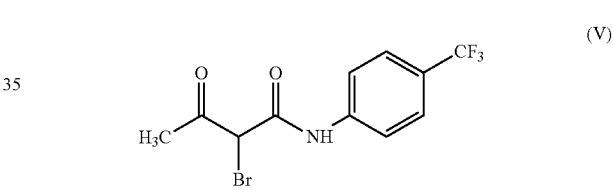
(I)

comprising steps of:
(i) condensing ethylacetoacetate (II)

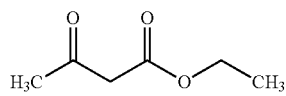
(II)

with 4-trifluoromethyl aniline (III) in a solvent

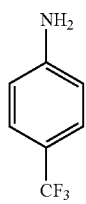

to give 3-oxo-N-(4-trifluoromethylphenyl)butanamide (IV);

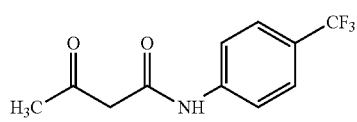

(ii) brominating 3-oxo-N-(4-trifluoromethylphenyl)butanamide (IV) with brominating agent optionally in presence of solvent to give 2-bromo-3-oxo-N-[4-(trifluoromethyl)phenyl]butanamide (V);

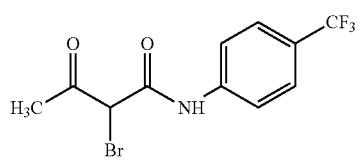

(iii) reacting 2-bromo-3-oxo-N-[4-(trifluoromethyl)phenyl]butanamide (V) with alkali cyanide in the presence of a solvent to give Teriflunomide (I).

The present invention provides a process for preparation of Teriflunomide. Ethylacetoacetate (II) and 4-trifluoromethyl aniline (III) is refluxed in a solvent. The solvent is selected from aromatic hydrocarbon such as toluene, xylene, nitrobenzene, benzene and the like or mixtures thereof. The reaction mixture is refluxed for about 48 hours. The Reaction mixture is concentrated and purified by column chromatography to give pure 3-oxo-N-(4-trifluoromethylphenyl)butanamide (IV).

3-oxo-N-(4-trifluoromethylphenyl)butanamide (IV) is reacted with brominating agent optionally in the presence of a solvent at room temperature. Brominating agents are selected from bromine, hydrogen bromide, N-bromosuccinimide, 4-(dimethylamino) pyridinium bromide perbromide and pyridinium hydrobromide. The solvent is selected from a group comprising chlorinated solvents, aromatic hydrocarbon. The example of a solvent includes but not limited to dichloromethane, dichloroethane, chloroform, carbon tetrachloride, toluene, xylene, nitrobenzene, benzene, cyclohexane and the like or mixture thereof. After completion of the reaction, D.M water is added to the reaction mixture and both aqueous and organic layers are separated. Aqueous layer is extracted with ethyl acetate. Combined organic layer is washed with brine solution, dried on sodium sulfate and distilled out to give 2-bromo-3-oxo-N-[4-(trifluoromethyl)phenyl]butanamide (V).

2-bromo-3-oxo-N-[4-(trifluoromethyl)phenyl]butanamide (V) is reacted with alkali cyanide such as sodium cyanide, potassium cyanide, lithium cyanide in a solvent at ambient temperature for overnight. The solvent is selected from DMSO, DMF, DMAc, sulfolane or mixtures thereof. After completion of the reaction, the reaction mixture is diluted with water and acidified with 50% HCl solution. The precipitated solid is filtered and washed with water and suck dried. The solid is dried to give Teriflunomide (I).

The synthetic reaction scheme of the present invention is as shown below in scheme-IV

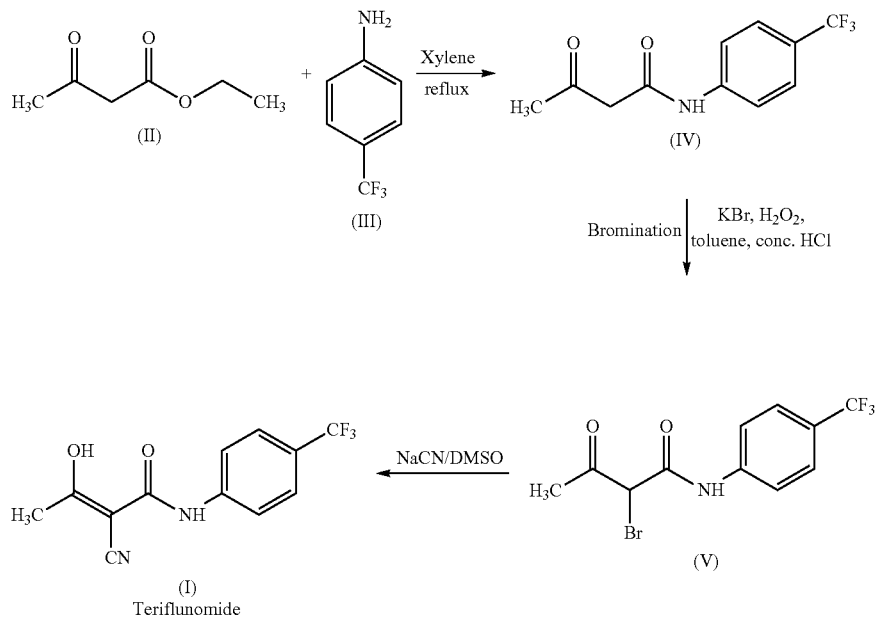

The following examples illustrate the invention further. It should be understood, however, that the invention is not confined to the specific limitations set forth in the individual examples but rather to the scope of the appended claims.

Example-1

Preparation of 3-oxo-N-(4-trifluoromethylphenyl)butanamide (II)

Ethylacetoacetate (10 g) and 4-(trifluoromethyl) aniline (12.38 g) in xylene (250 ml) was refluxed for 48 hours. Reaction mixture was concentrated and purified by column chromatography to give pure (9.7 g).
Yield: 51.4%

Example-2

Preparation of 2-bromo-3-oxo-N-[4-(trifluoromethyl)phenyl]butanamide (III)

Hydrogen peroxide (8.096 ml) was added dropwise to the well stirred solution of 3-oxo-N-[4-(trifluoromethyl)phenyl] butanamide (10 g) [obtained from above step-a], potassium bromide (4.85 g) and conc. HCl (7.446 ml) in toluene (100 ml) at room temperature. Reaction was monitored by TLC. D.M water was added to the reaction mixture and organic layer was separated. Aqueous layer was extracted with ethyl acetate (50 ml×2). Combined organic layer was washed with brine, dried over sodium sulfate and concentrated to give crude compound. The crude was purified by column chromatography to give pure 2-bromo-3-oxo-N-[4-(trifluoromethyl) phenyl]butanamide (6.4 g).
Yield: 67.0%

Example-3

Preparation of Teriflunomide

A mixture of 2-bromo-3-oxo-N-[4-(trifluoromethyl)phenyl]butanamide (10 g) [obtained from above step-b] and sodium cyanide (1.69 g) in DMSO (30 ml) was stirred at room temperature overnight. The reaction mixture was diluted with water (100 ml) and acidified with 50% HCl solution. Precipitated solid was filtered and washed with water. The solid was dried to give Teriflunomide (7.12 g).
Yield: 85.4%
$^1$HNMR (DMSO, 300 MHz): δ 2.27 (s, 3H); 7.25 (bs, 1H); 7.66 (d, J=8.64 Hz, 2H); 7.77 (d, J=8.61 Hz, 2H); 10.72 (s, 1H) ppm.
$^{13}$CNMR (DMSO, 75 MHz): δ 23.91, 81.7, 119, 121.9, 124.6, 126.7, 126.9, 142.4, 167.2, 187.8 ppm.
Mass: 269 (M$^+$−1).
IR: 3305, 2220, 1633, 1596, 1554, 1418, 1405, 1325, 1247, 1114, 1157, 1073, 971, 842, 684 cm$^{-1}$.

We claim:
1. A process for preparation of Teriflunomide (I)

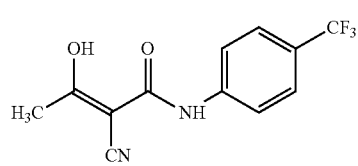

comprising steps of:
(i) condensing ethylacetoacetate (II)

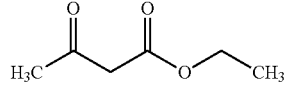

with 4-trifluoromethyl aniline (III) in a solvent

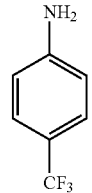

to give 3-oxo-N-(4-trifluoromethylphenyl)butanamide (IV);

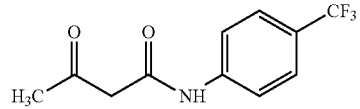

(ii) brominating 3-oxo-N-(4-trifluoromethylphenyl)butanamide (IV) with brominating agent optionally in presence of a solvent to give 2-bromo-3-oxo-N-[4-(trifluoromethyl)phenyl]butanamide (V);

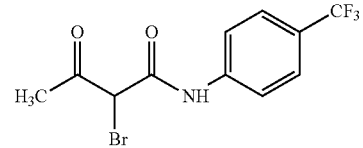

(iii) reacting 2-bromo-3-oxo-N-[4-(trifluoromethyl)phenyl]butanamide (V) with alkali cyanide in the presence of a solvent to give Teriflunomide (I).
2. The process as claimed in claim 1, wherein the solvent for step (i) is selected from aromatic hydrocarbons such as toluene, xylene, nitrobenzene, benzene or mixtures thereof.
3. The process as claimed in claim 1, wherein brominating agent is selected from bromine, hydrogen bromide, N-bromosuccinimide, 4-(dimethylamino) pyridinium bromide perbromide and pyridinium hydrobromide or mixtures thereof.
4. The process as claimed in claim 1, wherein the solvent for step (ii) is selected from chlorinated solvents, aromatic hydrocarbons such as dichloromethane, dichloroethane, chloroform, carbon tetrachloride, toluene, xylene, nitrobenzene, benzene, cyclohexane or mixtures thereof.
5. The process as claimed in claim 1, wherein alkali cyanide is selected from sodium cyanide, potassium cyanide, hydrogen cyanide or mixtures thereof.
6. The process as claimed in claim 1, wherein the solvent for step (iii) is selected from DMSO, DMF, DMAc, sulfolane or mixtures thereof.
7. A compound of formula (V)

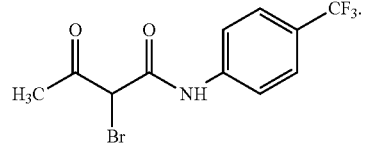

* * * * *